(12) United States Patent
Barabash et al.

(10) Patent No.: US 6,352,510 B1
(45) Date of Patent: Mar. 5, 2002

(54) ULTRASOUND TRANSDUCERS FOR REAL TIME TWO AND THREE DIMENSIONAL IMAGE ACQUISITION

(76) Inventors: Leonid S. Barabash, 15226 S. Power Rd., Apt. 2006, Higley, AZ (US) 85236; Aaron E. LaBarge, 3910 Carmel Spring Way, San Diego, CA (US) 92130; Gregory W. Saxell, 19447, E. Via de Olivos, Queen Creek, AZ (US) 85242; Angel T. M. Wang, 391-G Cannon Green Dr., Goleta, CA (US) 93117

(*) Notice: Subject to any disclaimer, the term of this patent is extended or adjusted under 35 U.S.C. 154(b) by 103 days.

(21) Appl. No.: 09/599,268

(22) Filed: Jun. 22, 2000

(51) Int. Cl.⁷ .................................................. A61B 8/00
(52) U.S. Cl. ........................................ 600/443; 128/916
(58) Field of Search ............................... 600/437, 441, 600/443, 447, 458, 459; 128/916; 73/602, 625, 626; 367/7, 11, 130, 138; 310/335

(56) References Cited

U.S. PATENT DOCUMENTS

| | | | | |
|---|---|---|---|---|
| 4,915,115 A | * | 4/1990 | Sasaki et al. ................ | 600/441 |
| 4,949,310 A | * | 8/1990 | Smith et al. .................... | 367/7 |
| 5,103,129 A | * | 4/1992 | Slayton et al. ............... | 310/335 |
| 5,148,810 A | | 9/1992 | Maslak et al. .......... | 128/661.01 |
| 5,797,845 A | | 8/1998 | Barabash et al. ............ | 600/443 |
| 5,842,991 A | * | 12/1998 | Barabash ..................... | 600/443 |
| 5,860,926 A | * | 1/1999 | Barabash et al. ............ | 600/443 |
| 5,901,708 A | | 5/1999 | Chang et al. ................ | 128/916 |
| 6,138,513 A | * | 10/2000 | Barabash et al. .............. | 73/602 |

OTHER PUBLICATIONS

Barabash et al., US Patent Application No: 09/228,028, Method and Apparatus for Fast Acquistion of Ultrasound Images, Filed Jan. 9, 1999.

L.S. Barabash et al., Silicon Two–Coordinate Detector With Separable Pad–Strip Readout, JINR Rapid Communications, 1[75]–96, Dubna, Russia.

S.W.Smith et al., Two–Dimensional Arrays for Medical Ultrasound, Ultrasonics Symposium, 1991, p. 625.

* cited by examiner

Primary Examiner—Marvin M. Lateef
Assistant Examiner—Ali M. Imam

(57) ABSTRACT

A present invention shows some schemes of a cross transducer with one transmit and one receive array for the three dimensional image acquisition. Designs of the cross transducer with and without a central shared element are described. Conditions for an extension of a frequency range and the method of an extended frequency range for use of the cross transducer are suggested. A new method of image formation allowed by the above is also presented.

12 Claims, 10 Drawing Sheets

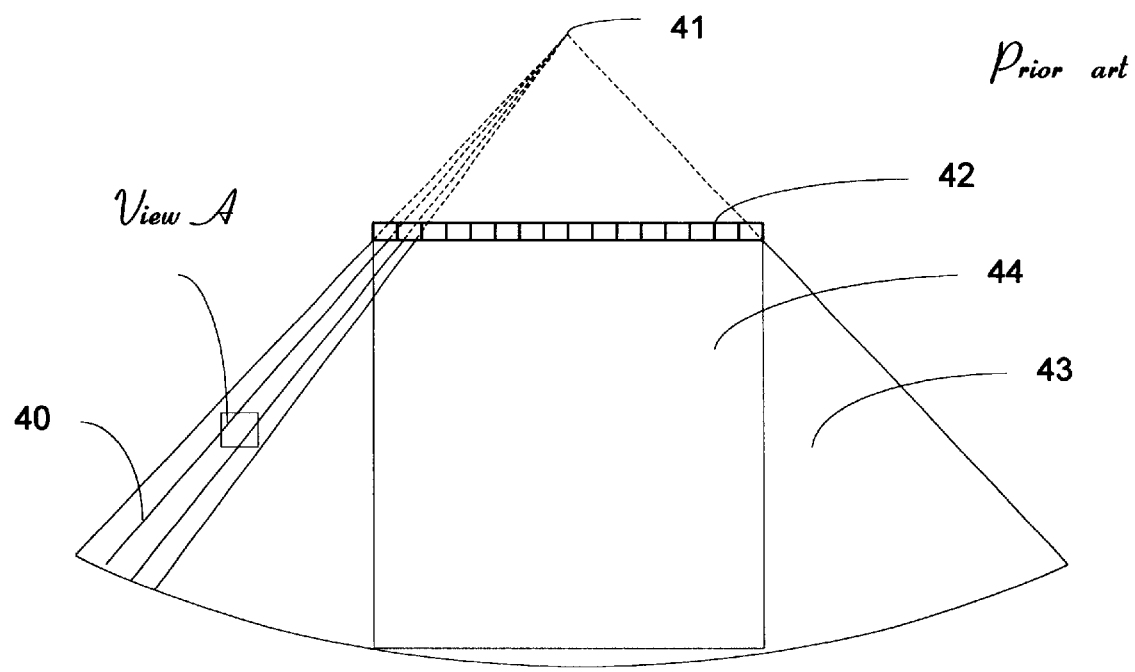
Figure 9.a
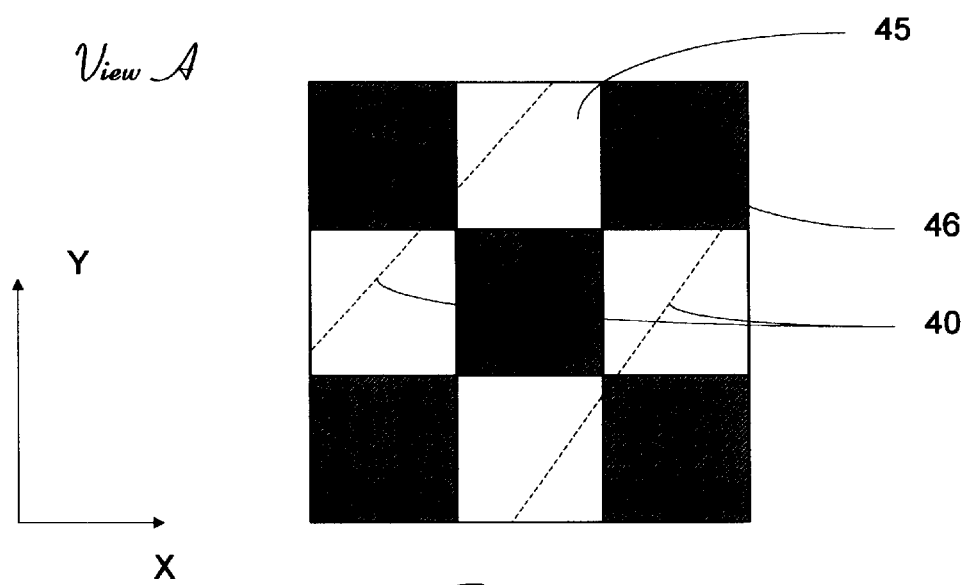
Figure 9.b

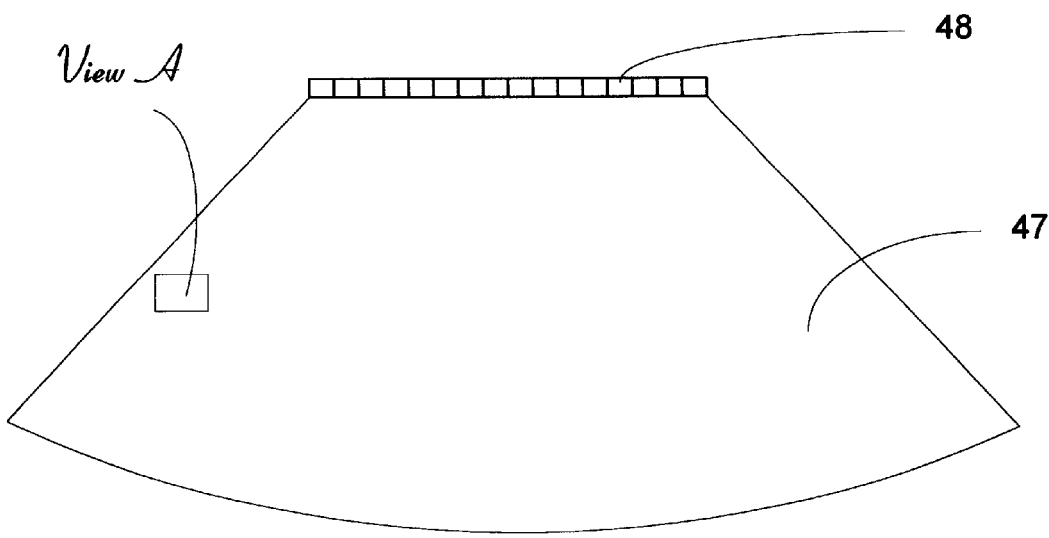
Figure 10.a
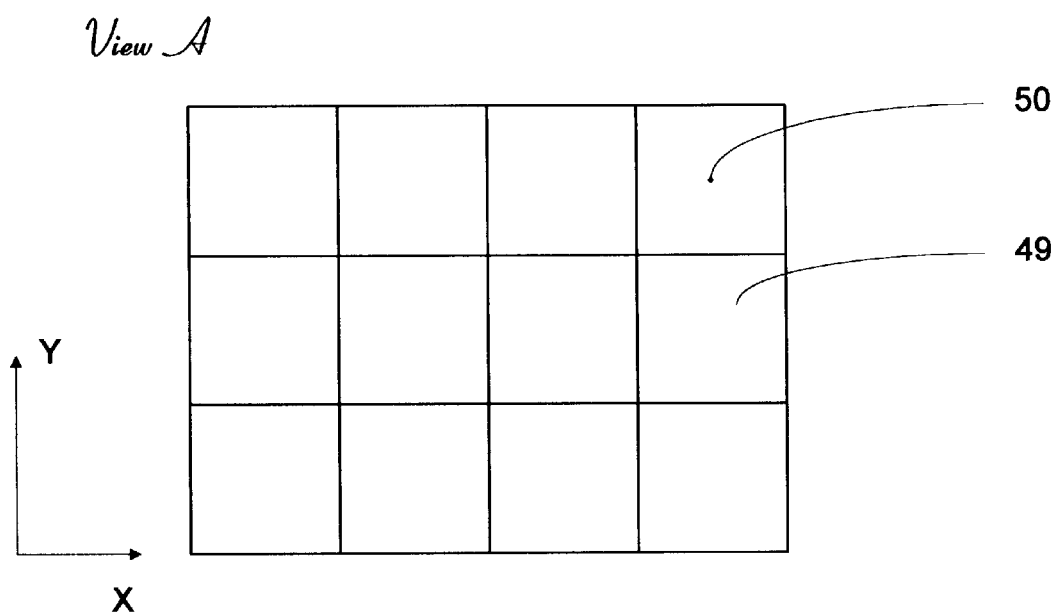
Figure 10.b

ULTRASOUND TRANSDUCERS FOR REAL TIME TWO AND THREE DIMENSIONAL IMAGE ACQUISITION

The present invention relates to an apparatus and methods for fast two and three dimensional ultrasound image acquisition, using a transducer design with cross geometry of a phased array placement which reduces the level of side lobe amplitudes and extends the useful frequency range of the transducers.

STATE OF THE ART

A problem of an acquisition of three-dimensional images is very important and allows one to increase the diagnostic ability of acoustic scanners. Very strong steps and progress were done in this direction by the use of transducers that mechanical steered the acoustic beam. It is seen very clear how strong these beautiful three-dimensional images increase the ability of diagnosis and treatment of patients. However, these are non-real time images.

Acquisition of real time three-dimensional images requires new fast methods of acquisition of acoustic images. Such methods are described in U.S. Pat. No. 5,797,845 of Barabash et al. This method employs an ability of a linear array with small individual elements to produce a flat acoustic beam or a flat receive aperture steered into some angle range. A cross placement of two linear arrays allows one to obtain a pencil acoustic beam by cross-section of the flat acoustic beam and the flat receive aperture, and an ability to steer the pencil acoustic beam into some solid angle limited by a radiation directivity of array individual elements. A creation of synthetic receive apertures by the use of digital beam-formation as shown in former schematics, allows a realization of a fast method of acquisition of three dimensional images by a fast steering of the flat acoustic apertures along the coordinate parallel to the direction of the receive array.

From all schemes of cross transducers suggested in this patent a scheme of a cross transducer with one transmit and one receive array is most attractive. In addition to properties described above, the use of this simple scheme significantly reduces the apparatus volume.

However, the shaping of a beam with a low level of side lobe amplitudes is a problem for this simple scheme. Both ways, first a transmission of acoustic waves and second a reception of echo signals participate in the process of side lobe amplitude reduction. But, the efficiency of the second way is not as high as the usual transducers used for two dimensional image acquisition, when both transmit flat beams and flat receive apertures produced by array individual elements are focused along the same plane.

The same method and schematics of a cross transducer are described in the U.S. Pat. No: 5,901,708 of Chang et al. Additionally specified, is the presence of a shared central element and a pitch of an array individual element equal to $\lambda/2$ of carrier frequency.

A problem of the shared element exists for a cross transducer with an odd number of transmit and receive array individual elements, and is absent when transmit and receive arrays have an even number of individual elements.

Another severe limitation of the use of this suggestion is specification of the pitch of array individual elements by $\lambda/2$ steps. It means that for any frequency which can be used by an acoustic scanner, we must have a separate transducer with the pitch of $\lambda/2$ for this frequency. For example, a most popular frequency range (2–10) MHz (2 MHz, $\lambda/2=0.385$ mm; 4 MHz, $\lambda/2=0.1925$ mm; 6 MHz, $\lambda/2=0.1283$ mm; 8 MHz, $\lambda/2=0.09625$ mm; 10 MHz, $\lambda/2=0.077$ mm) usually covered by two transducers approximately must be covered by five transducers. It is necessary to point out here that the most expensive parts of any acoustic machine are the transducers. Every transducer has its own frequency range defined by a mechanical and an electrical design. Many patents and published articles are dedicated to efforts that extend the frequency range of transducers; the main reason being is to reduce the price of acoustic machines and to increasing the number of transducers is more costly.

Specification for the pitch of arrays of $\lambda/2$ in acoustic technology is historically based on radar and sonar technologies. But, let us remember the main conditions when this rule is applicable:

Placement of array elements with the pitch P is equal to:

$$P = \lambda(n + \tfrac{1}{2})$$

where $\lambda$ is the wave length for the carrier frequency and $n=0, 1, 2, 3, \ldots$.

The lens is flat and is used for the shaping of a parallel beam. A difference in delays between adjacent individual elements is equal to 0 and a phase shift between individual elements of the array provided by the specified placement is $\pi, 3\pi, 5\pi, \ldots$ The duration $\tau_{tr}$ of the transmitted pulse is long:

$$\tau_{tr} \gg T,$$

where T is a period of the carrier frequency and the usual requirement is $\tau_{tr} > 100T$.

An amplitude of side lobes in the direction normal to the beam has a resonance behavior and is minimal when the pitch of array individual elements is $\lambda(n+\tfrac{1}{2})$ of the carrier frequency.

However, all these conditions are violated when the acoustic beam is shaped. Wave packages transmitted by transmit array individual elements are short to provide good space resolution; the beam shaped by the array has a definite focus; lenses which are used for the focusing of the acoustic beam are curved. It is impossible to satisfy the main condition (phase shift between adjacent array individual elements is $\pi, 3\pi, 5\pi, \ldots$) which provides a destructive superposition of waves and a low level of side lobe amplitudes, because delays of array individual elements are changed from one element to another and a difference between delays of adjacent elements is not equal to 0, especially for large beam scan angles.

An additional effect, which influences the position and amplitude of the side lobe, is the spherical shape of the wave packages emitted by a separate array individual element. They are crossed in the focus and provide the shaping of the main lobe. But the shape of wave packages have noticeable curvature for a reasonable value of F-numbers. Therefore, all array elements participate in the shaping of the main lobe and low level of side lobe amplitudes in the vicinity of the main lobe. The number of array elements along a scan line that participate in the shaping of the side lobe level is decreased for azimuth angles far away from the focus, and the level of side lobes begins to grow. The width of the zone when all array elements provides the shaping of the low level of side lobes near the main lobe depends on the duration of the pulse emitted by transducer elements.

SUMMARY OF INVENTION

Thus, it is the intent of the present invention to show schemes of a simple cross transducer with one transmit and one receive array which has no problem of a shared central element.

Another intent of the present invention is to show versions of cross transducers with a shared central element, but the design of the central crossing area allows one to separate transmit and receive returns and increase the signal-to-noise ratio.

We would like to present a method of the use of cross transducers for acquisition of real time two and three dimensional images, which allows an extension of a frequency range and an efficient use of cross transducers and the increase of the range of beam scan angles.

In particular, this method includes the next steps:

An optimal choice of the pitch of transmit and receive array individual elements to provide an extension of the dynamic range of frequency for the cross transducer.

An optimal choice of the duration of transmitted pulses used for irradiation of an investigated object providing an increase of the dynamic range of beam scan angles.

An optimal processing of digitized echo signal amplitudes to provide a correction of amplitudes of echo signals depending on the scan angle to reduce an influence of the directivity of the array individual elements radiation and provide a uniform brightness of images.

An optimal processing of digitized echo signal amplitudes to provide a reduction of side lobe amplitudes based on a knowledge of a behavior of side lobe amplitudes depending on the position of voxels used for a creation of three dimensional images in the investigated space. The reduction of side lobe amplitudes can be done by the correction of side lobe amplitudes. A correction function can be defined by a simulation or measurements of side lobe amplitudes with a consequent normalization and deduction of them by an iteration process from amplitudes of other voxels placed on the same spherical surface.

Another method of a reduction of side lobe amplitudes for two dimensional image acquisition is presented. The sense of this method is an asymmetry in the position of array individual elements when they are grouped in three groups: two groups have positive and negative shifts along the lateral coordinate and one group non-shifted elements. Non-shifted elements can be used as transmit array elements (or receive elements) and groups of shifted elements can organize array for the reception (or transmission) of echo signals. Such an asymmetry provides an additional phase shift of transmit packages or received echo signals for area far away from the main lobe and reduces the level of side lobe amplitudes significantly.

The same effect of a suppression of the side lobe amplitudes is recognized for the simple cross transducer with one transmit and one receive arrays when they are shifted relatively each other for a distance is equal to ¼ of the pitch.

The extension of the frequency range and the range of the beam scan angles allows the increase of the transducer field of view. An approach to the creation of the two and three dimensional images and the image format is described also.

BRIEF DESCRIPTION OF THE DRAWINGS

The preferred embodiments are described with reference to the drawings wherein:

FIG. 9 shows the prior art image format with the extended field of view.

FIG. 10 presents an example of transducer field of view described in the present invention.

DESCRIPTION

Figure 1:
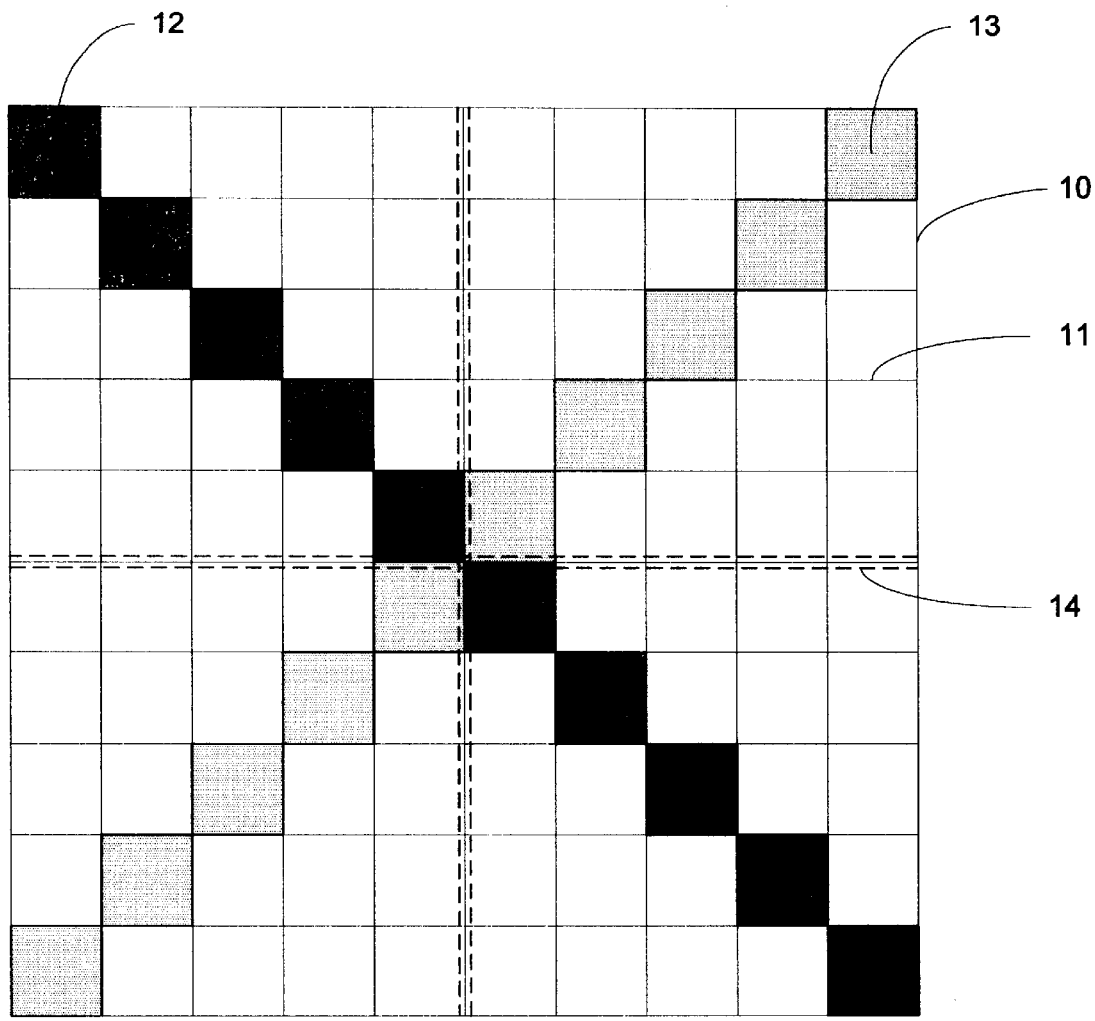
FIG. 1 shows an exemplary view of a simple cross transducer with an even number of transmit and receive array individual elements without a shared central element.

As we wrote above, the problem of a shared element exists for a cross transducer with an odd number of individual elements of arrays. We can avoid this problem by the use a design of arrays when the number of individual elements is even. The principles described by L. S. Barabash et al. in the article "Silicon Two—Coordinate Detector with Separable Pad—Strip Readout" (JINR Rapid Communications, No.1 [75]-96, p. 113–122, Russia) can be used to build such a design. The same principle of the shape of crossed arrays is shown by S. W. Smith et al., in the article "Two Dimensional Arrays for Medical Ultrasound" (1991, Ultrasonic Symposium, p. 625–628). FIG. 1 shows an exemplary view of a cross transducer design, which uses the principle of a "chess board". The transducer is built on the square shape of a piezo electric substrate 10. The substrate 10 is cut by grooves 11 and forms a matrix of square individual elements with an even number of rows and columns. Diagonal elements are used to form transmit array 12 and receive array 13. The separation of transmit and receive returns can be done by the grooves 14 placed on the opposite ground side of the piezo electric plate 10 with a join of diagonal transmit and receive returns into common transmit and receive grounds by external mounting.

Figure 2:
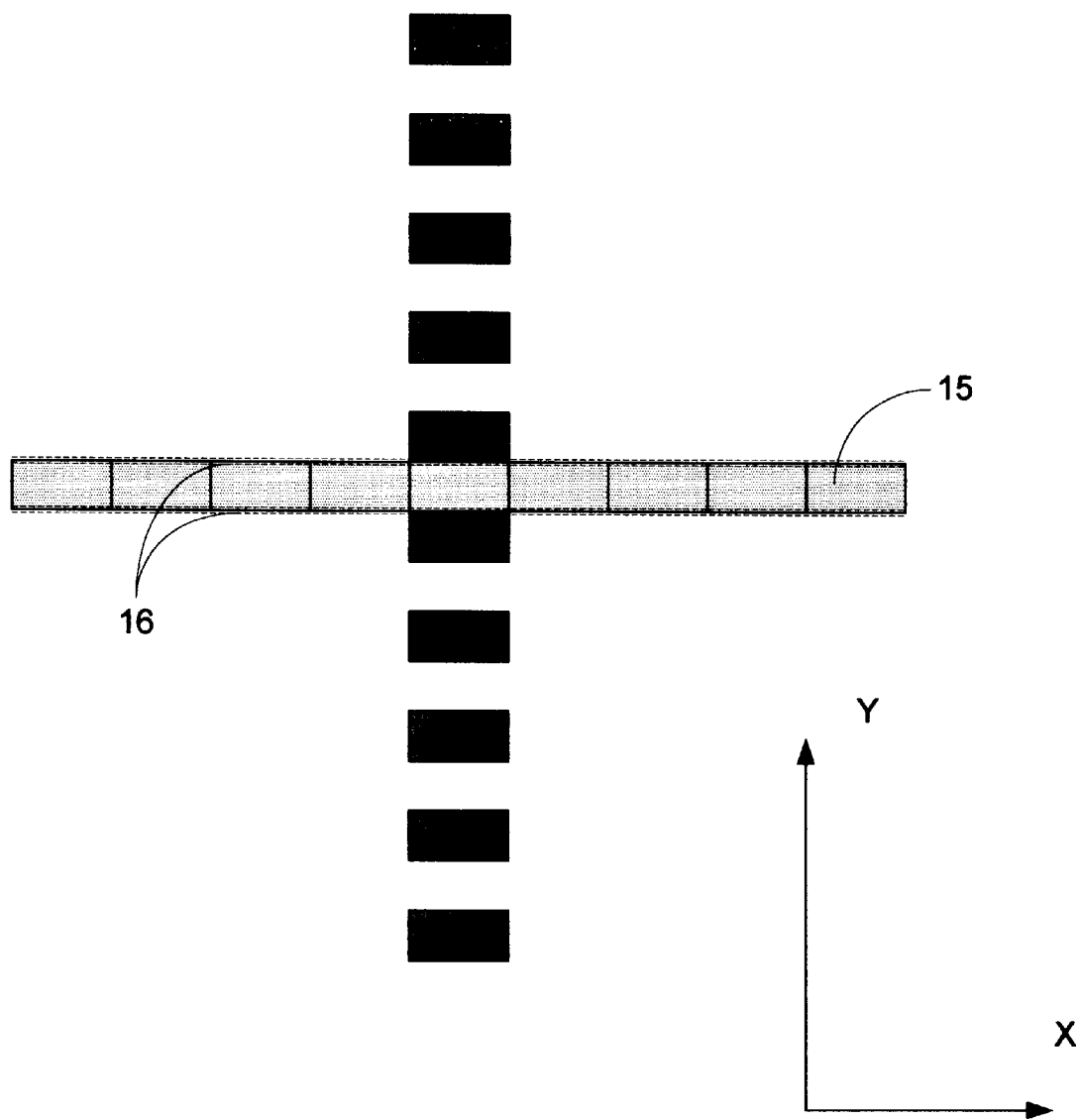
FIG. 2 presents an exemplary view of a cross transducer with a rectangular shape of array individual elements.

Another exemplary view of a cross transducer without a shared element is presented in FIG. 2. Individual elements 15 of arrays have a rectangular shape and are elongated along one coordinate. One of the arrays has an even number of individual elements, another has an odd number of individual elements. The cross transducer will have a different dynamic range of beam scan angles for different coordinates in this case. It will be wider along coordinate Y and narrower along coordinate X. This scheme allows the separation of transmit and receive returns by the cut of the grooves 16 on the opposite side of the piezo electric substrate. An additional possibility to solve a problem of a shared element in such a design is using a different pitch of transmit and receive array individual elements.

Figure 3:
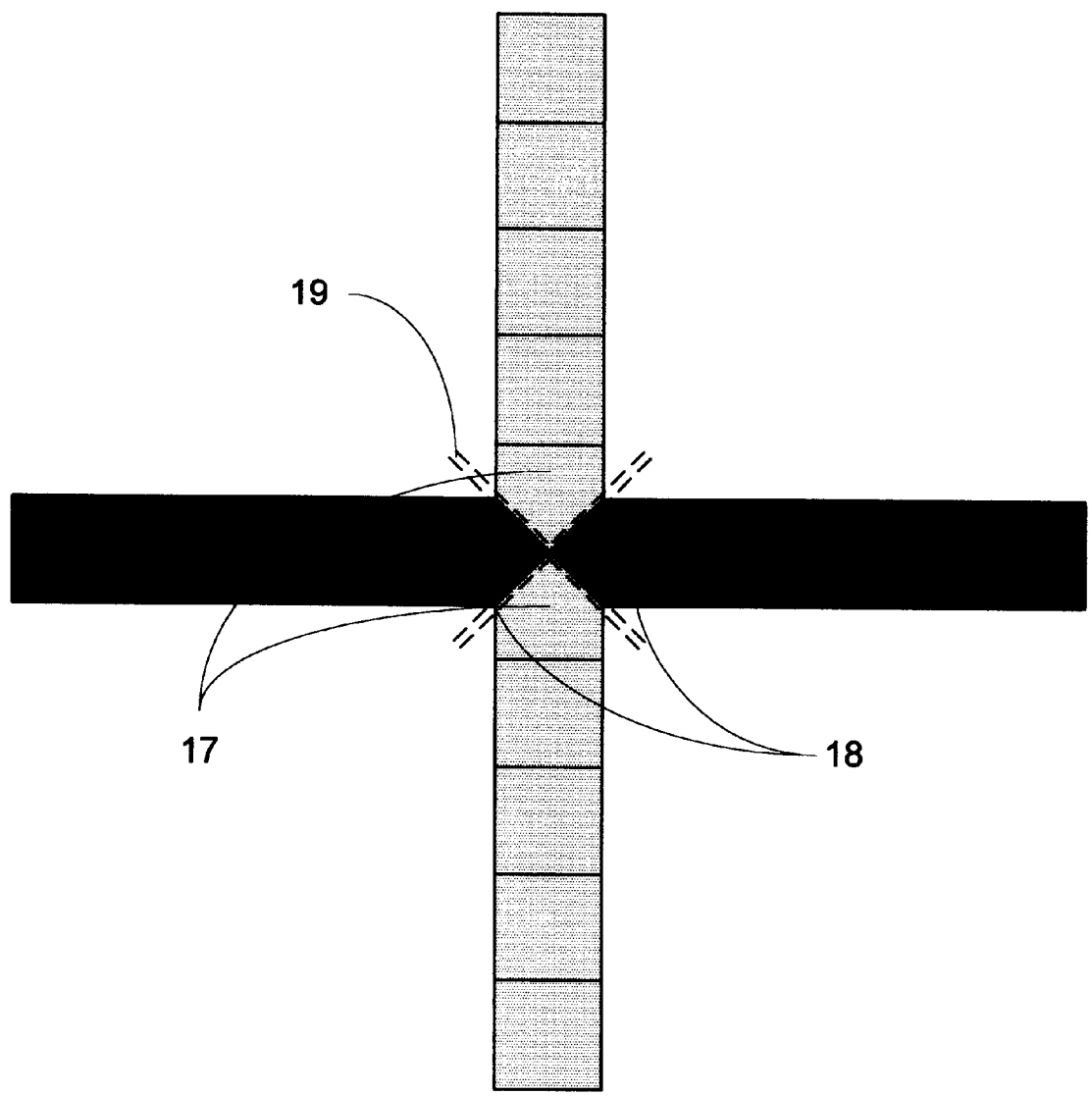
FIG. 3 shows an exemplary view of a cross transducer with an odd number of transmit and receive array individual elements and a complex crossed area.

FIG. 3 presents the exemplary view of a cross transducer with even number of array individual elements and a complex crossing area. Central pairs of transmit 18 and receive 19 individual elements are cut and isolated from each other along a direction of ±45° relative to the direction of transmit and receive array placement. The area of central individual elements 17 and 18 is smaller than the area of other array individual elements and requires a correction of amplitudes emitted by transmit elements 18 and echo signal amplitudes registered by receive individual elements 17. This design allows the separation of transmit and receive returns also by the grooves 19 which can be cut on the opposite ground side of the piezo electric substrate.

Figure 4:
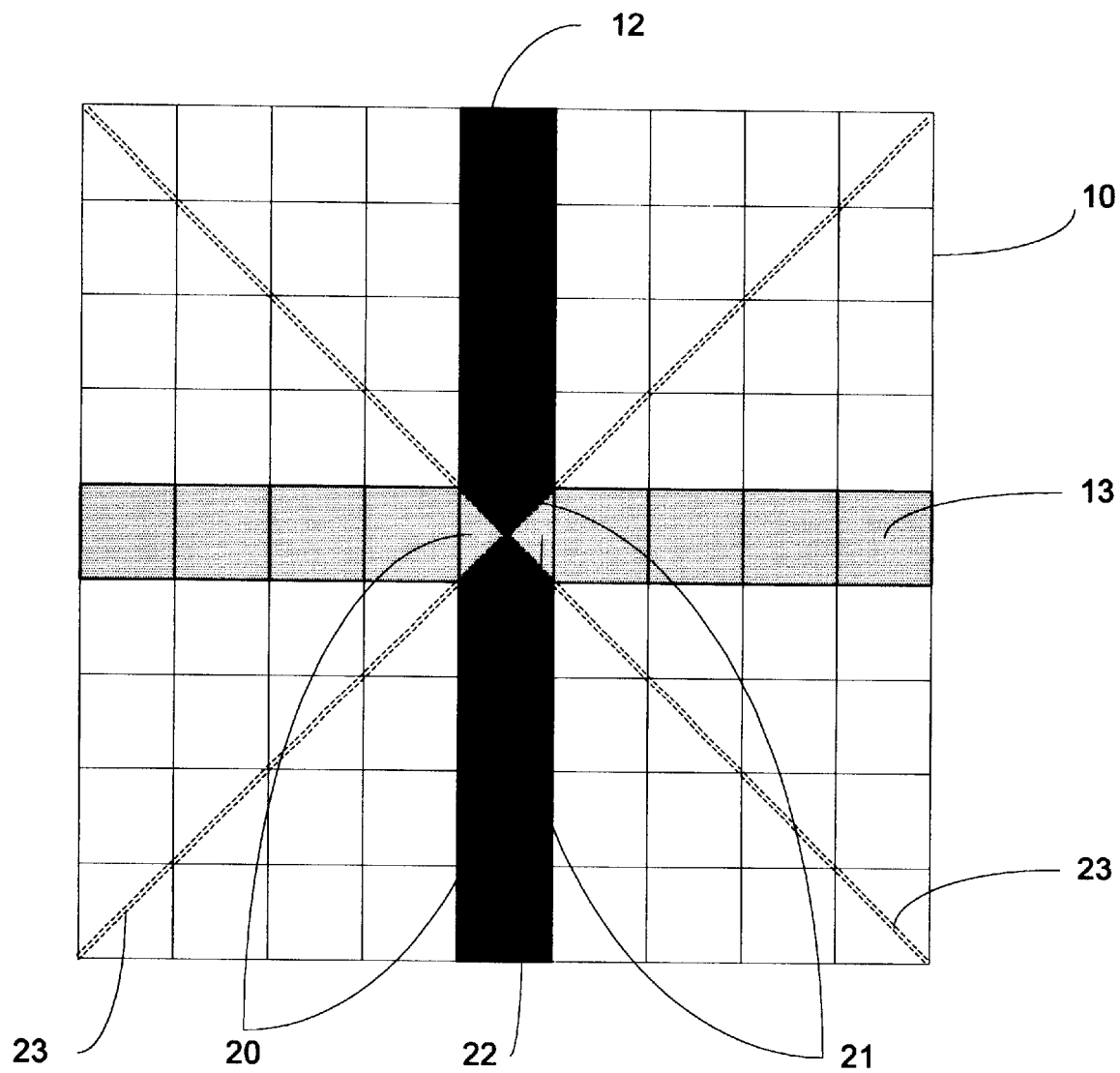
FIG. 4 presents a view of a cross transducer with an odd number of array individual elements and a sectioned-shared central element.

The view of a cross transducer with a shared central element is shown in FIG. 4. The transducer is made on the square piezo electric substrate as a matrix with an odd number of transmit 12 and receive 13 arrays individual elements placed along the central column and the central row. The central individual element is divided in four parts by grooves cut along its diagonals. Signal electrodes of opposite parts 20 and 21 are joined by the external mounting and form the central receive and the central transmit elements with a sensitive area lower than other individual array elements 22 by two times. Such a design also allows the separation of transmit and receive returns by the cut of the grooves 23 on the opposite ground side of the piezo electric substrate 10. This design requires the correction of transmit pulse amplitudes from pulse drivers and receive echo signals for transmit and receive parts of the central element. One of the ways is to leave the transmit pulse amplitude for central parts 21 the same as for other transmit individual elements, and increase the conversion gain of an electronic channel of the individual element 20 by four times. This type of correction (the increase of the conversion gain of a channel) can be done during the signal processing into a computer without a change of hardware.

Figure 5:
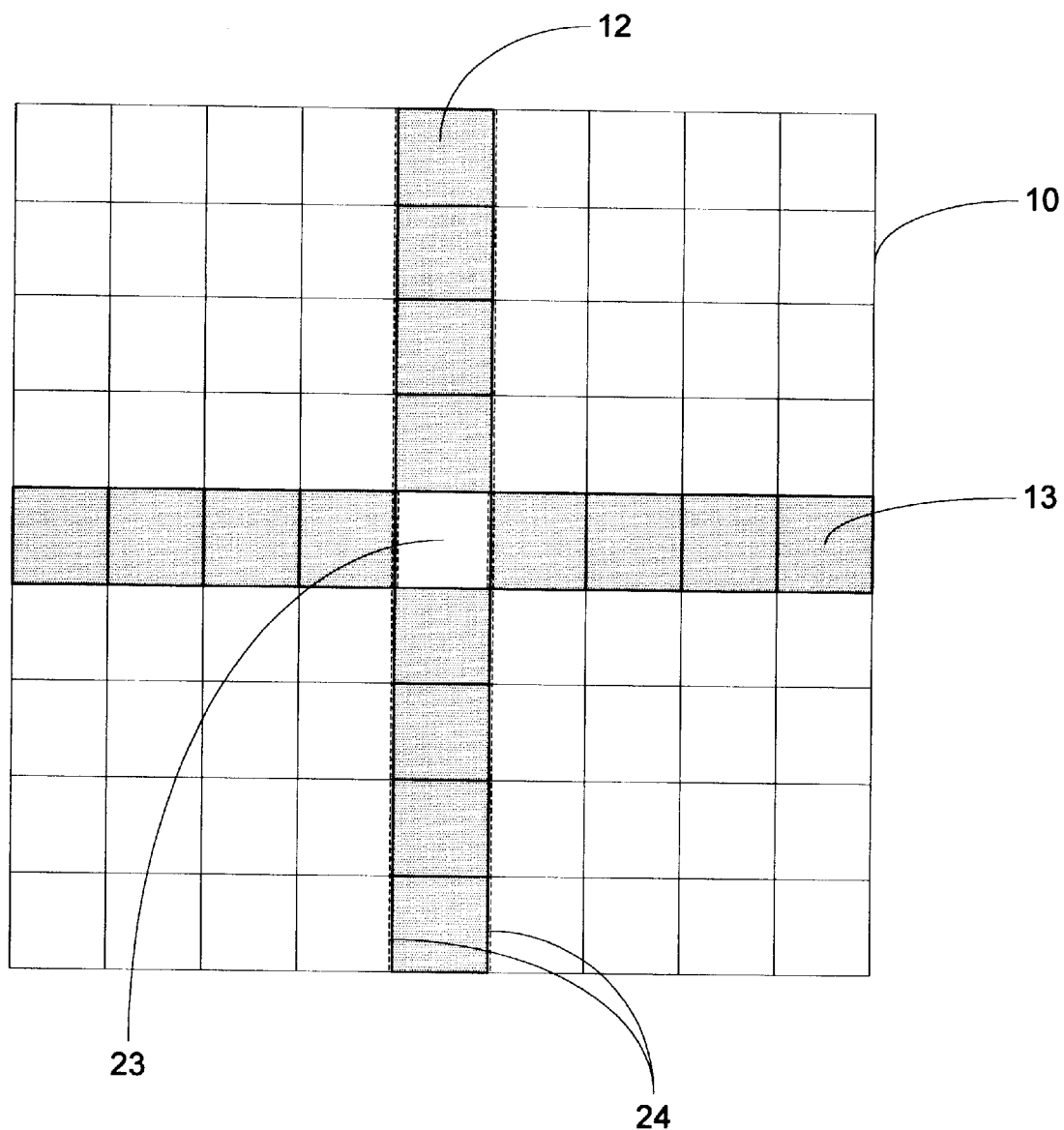
FIG. 5 shows a view of a cross transducer with an odd number of array individual elements and a shared central element, which has a ground electrode joined with the transmit return.

FIG. 5 shows a cross transducer design with an odd number of individual elements for transmit and receive arrays. The transmit array 12 is made as the central column of the matrix and the receive array 13 is made as the central row of the matrix. They have the shared central element 23. Transmit return separated from receive return by grooves 24 are cut on the opposite ground side of piezo-electric substrate 10. The ground electrode of the central shared element 23 is joined with transmit return. The electronic channel used for registration of the echo signals from the central shared element 23 has common return with a transmit part of the apparatus and is joined with the receive ground under the analog digital converter used for analysis of echo signal amplitudes from the central shared individual element 23. This connection of transmit and receive returns allows us to minimize a noise contribution of the central individual element electronic channel. Another method of separation of transmit and receive returns is using a transformer in the central individual element electronic channel.

The use of cross transducers allows the realization of fast acquisition of three dimensional images by the use of synthetic transmit and receive apertures. The next very important feature of any transducer is field of view. This parameter is defined by the pitch and the size of array individual elements. The admissible beam scan angle range for different sizes of the array individual elements varies and depends on the directivity of radiation of the individual element for a selected carrier frequency.

The size of the array individual element is almost equal to the pitch in order to realize a maximal emitted acoustic power. It is always slightly lower than the pitch of the placement of elements to provide a gap for isolation from each other. So, below, we will use a term of "pitch" as a definition for the size of the array individual element.

Two main parameters, which define a quality of images and a dynamic range of beam scan angles, are the amplitude of the main lobe and a distance to the maximal side lobe amplitude position, measured in the azimuth angle, depending on the ratio between the pitch of array individual elements and the wave length $\lambda$ of the carrier frequency. Both these parameters are reduced with the increase of the pitch of array individual elements for a selected carrier frequency. The distance between the main lobe and the maximum of the side lobe for the array with pitch P is changed from 80°–85° for frequencies with wave length $\lambda \sim (10-5)P$ to 25°–30° for frequencies with $\lambda \sim (0.6-0.7)P$. Simultaneously, the main lobe amplitude is reduced and the admissible beam scan dynamic range changes within the limits of the same angles as shown above.

Therefore, a cross transducer with pitch P can in fact be used with a broad range of frequencies with the wave length $\lambda$ from $\lambda \sim (5-10)*P$ to $\lambda \sim (0.6-0.7)*P$ including the case when $\lambda = 2*P$ (or $P = 0.5*\lambda$).

There is an almost linear dependence from the frequency versus the pitch of array individual elements. A parameter that defines a violation of "$\lambda/2$ rule" is the curvature of lenses used for the transmission of acoustic wave packages and for the reception of echo signals. A distribution of differences of delays between adjacent array individual elements for the shaping of lens, defines a level of the violation of "$\lambda/2$ rule". This is a clear geometrical parameter that depends on the pitch of array individual elements and position of the lens focus, and doesn't depend on the frequency. This parameter influences the position of side lobe amplitudes because it defines a deflection of an absolute value of wave phases for different individual elements from values of $\pi, 3\pi, \ldots$, when the best condition in the side lobe amplitude rejection is provided. The level of violation of the "$\lambda/2$ rule" and position of the side lobe, respectively, depend on the ratio of this parameter to the period of carrier frequency for a given pitch of array individual elements. This is a smooth dependence without any resonance phenomena. The ratio is small for low frequencies and the side lobe occurs with large azimuth angles. An increase of the frequency increases the deflection of wave phases from $\pi, 3\pi, \ldots$ and the azimuth angle between the position of the side lobe and the main lobe is decreased.

The choice of the frequency range for the cross transducer with pitch of P depends on the applications and should be optimized for two parameters such as the dynamic range of beam scan angles and the level of acoustic power.

Another parameter that has to be optimized is the duration of the emitted acoustic wave package. The width of the side lobe depends on the duration of emitted acoustic pulses. It is wide for short pulses and limits the dynamic range of beam scan angles. The increase of the acoustic pulse duration decreases the width of the side lobe. Therefore, optimization has to be done between the dynamic range of beam scan angles and the necessary time resolution, which decreases with the increase of the duration of the emitted acoustic package.

Two factors limit the beam scan angle range. These are the presence of side lobes and the reduction of the main lobe amplitude during scanning. Both factors, as we showed before, depend on the directivity of array individual elements for the selected carrier frequency.

Acquisition of three-dimensional acoustic images includes the calculation of wave vector values for every volume element (voxel) of the irradiated solid angle of the investigated object. The size of voxels depends on the resolution and can be done more rough in the real time scale. More detail analysis and precise calculation of wave vectors can be fulfilled by non-real time procedures.

Corrections of wave vector amplitudes for every voxel can be done multiple ways. One is described in patent application Ser. No. 09/228028 of Barabash et al. We would like to present here another method of correction of the calculated wave vector values.

Calculation of the wave vector value for every voxel has to be done under conditions that the synthetic transmit and receive apertures are focussed in this voxel volume. After calculation of the wave vector value, we can predict amplitudes of wave vectors defined by side lobe amplitudes for other voxels placed on the same spherical surface. This prediction is based on the knowledge of behavior of side lobe amplitudes in dependence on the position of the acoustic beam obtained from simulations or measurements. Another base point of these corrections is that the resolution provided by focused acoustic beam is always better than the washed out image provided by side lobes.

The time of calculation of corrected wave vector amplitudes for other voxels can be reduced by the use of some threshold, when corrections are made only for amplitudes which are more than this threshold value do the corrections have a sense.

The main lobe amplitude corrections can be done by the use of an approximation function symmetrical near the position of the acoustic beam with scan angle equal to 0.

Figure 6:
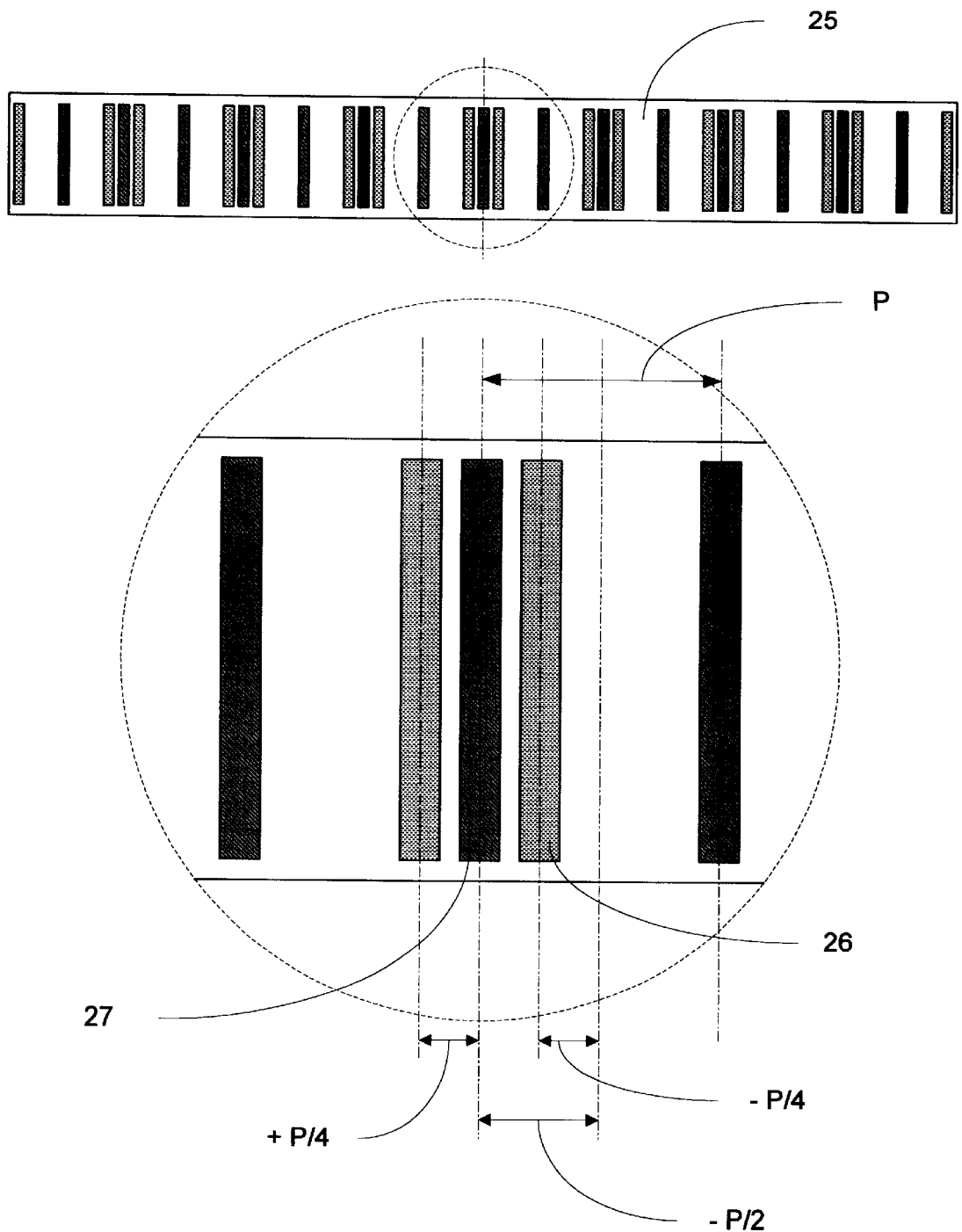
FIG. 6 presents an exemplary view of the transducer design for two dimensional image acquisition.

Another method of reduction of side lobe amplitudes for transducers used for two dimensional and three dimensional image acquisition is an asymmetry of a placement of transmit and receive arrays. Exemplary view of such a design of transducer for two dimensional image acquisition is shown at FIG. 6. Individual elements of the transducer array 25 have been divided into two groups. Array individual elements 27 of the first group are placed along the lateral coordinate with a pitch of P. Array individual elements 26 of the second group are placed between the array individual elements 27 of the first group by such a way when every other individual element of the second group is shifted along the lateral coordinate for a distance of −P/4 and other individual elements of the second group are shifted for a distance of +P4.

As a result, we obtain a group of non-shifted elements 27 and a group of shifted elements 26 with pitch between adjacent elements equal to 0.5P and 1.5P. Such a placement of array individual elements provides an additional phase shift of transmitted wave packages and received echo signals and allows one to reduce the level of side lobe amplitudes significantly.

The above results in suppression of side lobe amplitudes almost independent from the operating frequency. This increases the frequency range of the transducer and improves the dynamic range of beam scan angles. The effect of the suppression of the side lobe is recognized when non-shifted elements are used in the transmission (or reception) mode and shifted elements are used in the reception (or transmission) mode only. Such a design of the transducer can be used with phased steering as well as aperture shifting type scanning.

Barabash et al. describe the cross transducer with more than one transmit and more than one receive arrays and with the reduced level of side lobe amplitudes in patent application Ser. No. 09/928,028. The reduction of the side lobe is reached by a specific placement of transmit or receive arrays when the distance between arrays L is defined as L=P(m+½), where P is the pitch of transmit or receive arrays and m=0, 1, 2, . . . A minimal number of transmit or receive arrays is equal to 2. The same effect of the side lobe amplitude reduction is recognized for the simple cross transducer with one transmit and one receive arrays.

Figure 7:
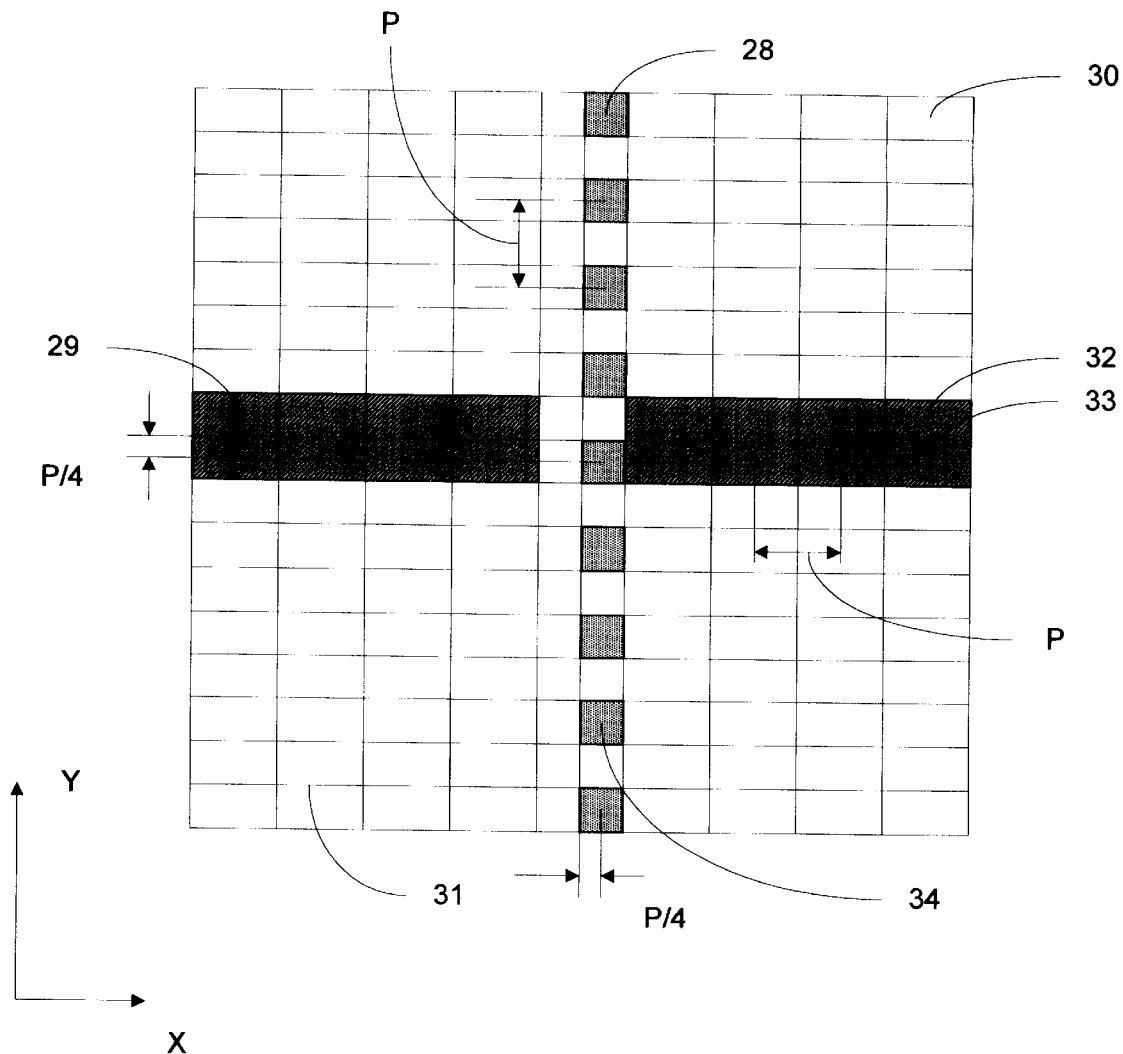
FIG. 7 shows a design of the cross transducer with arrays shifted relatively each other for a distance ¼ of the pitch along both coordinates.

FIG. 7 shows an exemplary view of the cross transducer with arrays 28 and 29 are made on the piezo-electric substrate 30. The separation of array individual elements is done by the grooves 31. Array 29 is comprised from individual elements 32 and 33 joined into square elements by the external mounting and has no the central element. The array 28 is comprised from individual elements 34 placed in the direction normal to the array 29. Individual elements of both arrays have a pitch of P. The position of the array 28 and the size of individual elements 34 are chosen by such a way that the array 28 is shifted relatively the center of the symmetry of the array 29 for a distance is equal to P/4 along both coordinates.

Figure 8:
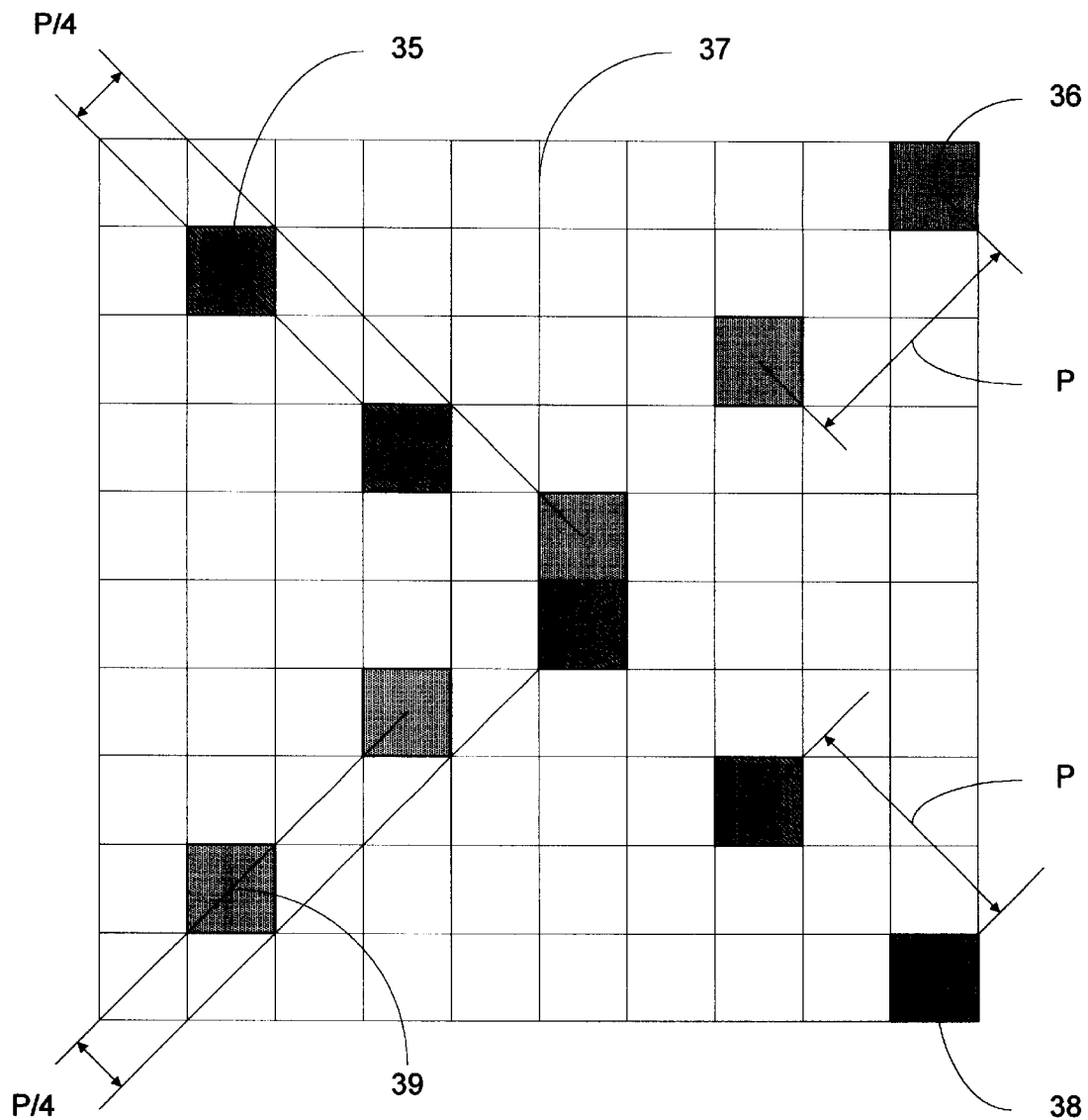
FIG. 8 presents another version of the cross transducer with arrays shifted for ¼ of the pitch.

FIG. 8 presents an exemplary view of the cross transducer with one transmit and one receive arrays 35 and 36 and with the same size of individual elements 38 and 39. Arrays 35 and 36 are made on the same piezo electric substrate 37 and have the same pitch of P. A position of arrays is chosen along diagonals of matrix by such a way that provides the shift of arrays along diagonal directions and relatively each other for a distance of P/4.

It is necessary to note that the shift of P/4 rejects the amplitude of the first side lobe. The reduction of the amplitude of the second side lobe requires the shift is equal to P/8.

We don't show designs with the shift of P/4 of one of the array. Such a design is simpler, but it provides the extension of the scan angular range of acoustic beam and the increase of the field of view of the transducer along one coordinate only.

A goal of this invention is the extension of useable frequency range of the transducer, as well as the increase of the angular range of the acoustic beam scanning to provide the maximum possible near and far field of view. FIG. 9 presents prior art image format described by Maslak et al. in U.S. Pat. No. 5,148,810. Main elements used to build an image are acoustic lines 40 that have the same common vertex 41 placed behind the transducer array 42 (FIG. 9.a.). The format of the image can be changed by the shift of the position of the common vertex 41 to provide the extended field of view 43 of the transducer in comparison with the usual field of view 44 for linear array. FIG. 9.b. (view A) shows details how the image is built. The direction of acoustic lines is coincided with the direction of the real acoustic beam emitted by the transducer array. Every acoustic line is combined from several parts registered from different acoustic beams emitted in the same direction with different foci. It limits the use of small F-numbers for transmit apertures because of the length of transmit zones, a fluctuation of the beam size and a time of the image acquisition. These limitations decrease the possible resolution of the acoustic scanner.

The transform of the image from the polar coordinate system into Decart coordinate system is done by the scan converter schematics. Two adjacent acoustic lines 40 are depicted. The pixels 45 of the image placed near the acoustic line contain measured amplitudes. The space between these pixels is filled by the pixels 46 that contain amplitudes obtained by an interpolation.

The concept of synthetic transmit apertures changes an approach to a creation of the acoustic images (Barabash et al., U.S. Pat. No. 5,860,926 and patent application Ser. No. 09/928,028). The real acoustic beam is absent. We work instead, with the virtual acoustic beam created by software tools. This beam and synthetic receive apertures can be focused at any point of image format with maximal array individual elements (part of array individual elements or all array individual elements) that can provide an effective contribution in the calculated amplitude of the wave vector for this point with the use minimal F-numbers for synthetic transmit and receive apertures. Obviously then, maximal resolution can be realized under such conditions. The image format can be the same as prior image format, but the principles used for creation of the image are completely different.

With concept of synthetic transmit and receive apertures the definition of "acoustic lines" has no sense. The main element used to build the image is "pixel" for two dimensional images or "voxel" for three dimensional images. As example, we show in FIG. 10.a. the image format 47 created by the linear transducer array 48. View A of FIG. 10.b. presents the detail view of the small part of the image. The image has pixels 49 placed in the rectangular coordinate system. The virtual acoustic beam created by the synthetic transmit aperture and the synthetic receive aperture are focused at the center 50 of every pixel. The value of the wave vector is calculated for every pixel without interpolation. Such an approach allows the use of the width of transmit and receive zones equal to or less than the time equivalent size of the pixel (or voxel). This is extremely important to get a low level of side lobe amplitudes. The same method of creation of images can be used for curved arrays also.

Data used for formation of images for prior art method are data obtained after a detection, a compression and demodulation filtration of signals before the image is built. All these stages of the analysis of data are made in a time scale. The method of image formation presented here supposes the first stage of image formation by the use non detected digitized radio frequency echo signals. A decision about detection and post detection analysis of data are made when the image is already built. So, all necessary stages of analysis are done with data distributed in the proper two or three dimensional space.

The format of images shown on the display screen can have any convenient geometric shape for recognition of the investigated object. It can be the image format shown at FIG. 10.a or some another shape. If this is a three dimensional image, any slice of the investigated volume with any direction and under any angle can be shown on the display screen. It is not limited to flat slices, even curved slices could be used to simultaneously image parts of the investigated object not in the same plane. An image format can be even more in this case than that provided by the field of view of the transducer.

We claim:

1. An ultrasound cross transducer with an extended range of beam scan angles for three dimensional image acquisition comprising:
    one transmit array having a plurality of individual elements is made on the piezo electric material substrate; said individual elements are connected with pulse drivers and provide only the emission of acoustic wave pulses into the investigated object,
    one receive array having a plurality of individual elements is made on said piezo electric material plate also, said individual elements are connected with only a reception apparatus, which provides the reception of the echo signals from the array individual elements, an amplification, a digitization, a memorization of echo signal amplitudes and a displaying of images,
    said transmit and receive arrays having axial symmetry with a common origin and oriented relative to each other for an angle equal to 90°,
    said transmit and receive arrays have a shared element if the number of said individual elements is odd and have no said shared element if the number of array individual elements is even,
    said transmit and receive arrays have a pitch P of array individual elements and are used within limits of frequencies with wave length $\lambda$ from $(10-5)*P$ to $(0.6-0.7)*P$.

2. An ultrasound cross transducer as recited in claim 1 having transmit and receive arrays are made on the square shape piezo electric substrate as diagonals of a matrix with an even number of columns and rows without a shared individual element.

3. An ultrasound cross transducer as recited in claim 2 having an opposite side of said piezo electric substrate is cut along the central lines for four quadrants, and diagonal quadrants are joined by an external mounting and used as transmit and receive returns.

4. An ultrasound cross transducer as recited in claim 1 having transmit and receive arrays with individual elements elongated along one coordinate, one of said arrays has an odd number of individual elements, another has an even number of individual elements and a pitch of transmit and receive array individual elements can be different.

5. An ultrasound cross transducer as recited in claim 1 having transmit and receive arrays with an even number of individual elements, the central pairs of said individual elements are cut and isolated from each other along a direction of ±45° relative to the direction of transmit and receive array placement, opposite the side of the piezo electric substrate is cut at the same direction by grooves to isolate transmit and receive returns.

6. An ultrasound cross transducer as recited in claim 1 having transmit and receive arrays with a shared central element is cut along diagonals in four triangles, opposite pairs of said triangles are joined by an external mounting and used as central transmit and central receive elements, an opposite side of the piezo electric substrate is cut at the same direction and opposite pairs of ground electrodes are joined and form transmit and receive returns.

7. An ultrasound cross transducer as recited in claim 1 having transmit and receive arrays with an odd number of individual elements and with a shared central element are made on the square piezo electric substrate as a central column and a central row of a matrix, the said central shared element has a common return with a transmit return isolated from receive array return, said common return is joined with said receive array return in consequent apparatus.

8. An ultrasound cross transducer as recited in claim 1 having transmit and receive arrays are made on the same piezo electrical substrate as central column and row of matrix, one array without a central element, individual elements of the second array have an area for four times smaller than individual elements of the first array and are shifted near center of the first array for ¼ of a pitch along both coordinates.

9. An ultrasound cross transducer as recited in claim 1 having transmit and receive arrays are made on the same piezo electrical substrate as diagonals of matrix with an even number of columns and rows and are shifted along diagonal directions for ¼ of a pitch.

10. A method of the use of a cross transducer to provide an extended frequency and angular beam scanning ranges comprising the following steps:
    providing a pitch P of transmit and receive array individual elements,
    using a cross transducer with a range of frequencies with the wave length $\lambda$ from $\lambda \sim (5-10)*P$ to $\lambda \sim (0.6-0.7)*P$, providing an increase of a dynamic range of beam scan angles by an optimal choice of a duration of transmitted acoustic packages used for irradiation of an investigated object, providing an optimal processing of digitized echo signal amplitudes with a correction of amplitudes of said echo signals depending on the beam scan angle, providing an optimal processing of digitized echo signal amplitudes with a reduction of side lobe amplitudes by a correction of wave vector values for voxels placed on the same spherical surface.

11. An ultrasound transducer for two dimensional image acquisition with an extended range of beam scan angles having:

a plurality of individual elements elongated along the elevation coordinate to provide mechanical focussing of acoustic beam along elevation coordinate, said plurality of individual elements are divided for two groups placed along lateral coordinate and are differed by the placement of array individual elements, said first group of array individual elements is placed along the lateral coordinate with a pitch P, said array individual elements of the second group are placed between the array individual elements of said first group, an every other individual element of the said second group is shifted along the lateral coordinate for a distance $-P/4$, other individual elements of said second group are shifted along the lateral coordinate for a distance $+P/4$, said first group of array individual elements is used in the transmission (or reception) mode and said second group of array individual elements is used in reception (or transmission) mode only to separate a transmit and a receive returns.

12. A method of an ultrasound image formation and displaying comprising the steps of:

providing an irradiation of an investigated object by a sequent excitation of transmit array individual elements, providing a reception of echo signals by receive array individual elements from every said transmit array individual element, an amplification of radio frequency echo signal amplitudes, a digitization of said radio frequency echo signal amplitudes and storage of them in a memory, shaping synthetic transmit and receive lenses focused at the same pixels (or voxels) with a maximal possible number of said transmit and receive array individual elements, providing a calculation of a wave vector value for every said pixel (or voxel) mapping of said wave vector values in a two dimensional space for two dimensional images and in a three dimensional space for three dimensional images, providing a detection of said radio frequency echo signals, providing a necessary post detection analysis of said two or three dimensional images, displaying said two or three dimensional images on the display screen with a generalized and arbitrary format convenient for fast recognition of objects of interest.

* * * * *